(12) United States Patent
Banik (10) Patent No.: US 11,040,149 B1
(45) Date of Patent: Jun. 22, 2021

(54) TAMPER EVIDENT CLOSURE ASSEMBLY FOR A MEDICAL DEVICE

(71) Applicant: Robert Banik, Ft. Lauderdale, FL (US)

(72) Inventor: Robert Banik, Ft. Lauderdale, FL (US)

(73) Assignee: INTERNATIONAL MEDICAL INDUSTRIES, Pompano Beach, FL (US)

(*) Notice: Subject to any disclaimer, the term of this patent is extended or adjusted under 35 U.S.C. 154(b) by 390 days.

(21) Appl. No.: 15/941,295

(22) Filed: Mar. 30, 2018

Related U.S. Application Data (60) Provisional application No. 62/478,867, filed on Mar. 30, 2017.

(51) Int. Cl.
| | |
|---|---|
| *A61M 5/50* | (2006.01) |
| *A61M 5/32* | (2006.01) |
| *A61J 1/14* | (2006.01) |
| *B65D 41/34* | (2006.01) |
| *A61M 5/31* | (2006.01) |
| *A61J 1/18* | (2006.01) |

(52) U.S. Cl.
CPC ........ *A61M 5/3202* (2013.01); *A61M 5/5086* (2013.01); *A61J 1/18* (2013.01); *A61M 5/3134* (2013.01); *B65D 41/3428* (2013.01)

(58) Field of Classification Search
CPC .............. A61M 5/5086; A61M 5/3202; A61M 2005/3104; A61M 39/1011; A61M 39/20; A61M 2039/1033; A61J 1/18; B65D 41/3428
See application file for complete search history.

(56) References Cited

U.S. PATENT DOCUMENTS

| | | |
|---|---|---|
| 732,662 A | 6/1903 | Smith |
| 1,678,991 A | 7/1928 | Marschalek |
| 1,970,631 A | 8/1934 | Sherman |
| 2,477,598 A | 8/1949 | Hain |

(Continued)

FOREIGN PATENT DOCUMENTS

| | | |
|---|---|---|
| EP | 0148116 A | 7/1985 |
| GB | 486367 | 6/1938 |

(Continued)

*Primary Examiner* — Manuel A Mendez
*Assistant Examiner* — Justin L Zamory
(74) *Attorney, Agent, or Firm* — Malloy & Malloy, P.L.; Jennie S. Malloy (57) ABSTRACT

A closure assembly for a medical device such as a syringe comprises a housing having an open end and a hollow interior. A tip cap is removably disposed within the housing and includes a cover connected to the open end by a snap-fit connection. An indicator ring includes an access opening and is removably connected to the cover in interruptive, removable restricting relation to said tip cap. The access opening is dimensioned to facilitate passage of the syringe therethrough into attachment with the tip cap, with the tip cap disposed into disconnecting engagement with said indicator ring concurrent to removal of said tip cap and attached syringe through said open end. Upon removal of the tip cap and attached syringe through the open end of the housing, the indicator ring will be disposed in a surrounding captured disposition on the syringe, thereby providing a clear indication of tampering or use.

26 Claims, 6 Drawing Sheets

(56) References Cited

U.S. PATENT DOCUMENTS

| | | |
|---|---|---|
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,368,673 A | 2/1968 | Johnson |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,747,751 A | 7/1973 | Miller et al. |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A * | 5/1987 | Vitello .............. A61M 5/5086 206/445 |
| 4,676,530 A | 6/1987 | Nordgren et al. |
| 4,693,707 A | 9/1987 | Dye |
| 4,726,483 A | 2/1988 | Drozd |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,049,129 A | 9/1991 | Zdeb et al. |
| 5,057,093 A | 10/1991 | Clegg et al. |
| D323,392 S | 1/1992 | Byrne |
| 5,135,496 A | 8/1992 | Vetter et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,380,295 A | 1/1995 | Vacca |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,375,640 B1 | 4/2002 | Teraoka |
| 6,394,983 B1 | 5/2002 | Mayoral et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,055,273 B2 | 6/2006 | Roshkoff |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |

(56) References Cited

U.S. PATENT DOCUMENTS

| | | |
|---|---|---|
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,443,999 B1 | 5/2013 | Reinders |
| D684,057 S | 6/2013 | Kwon |
| 8,512,277 B2 | 8/2013 | Del Vecchio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,082,157 B2 | 7/2015 | Gibson |
| 9,101,534 B2 | 8/2015 | Bochenko |
| D738,495 S | 9/2015 | Strong et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh et al. |
| D831,201 S | 10/2018 | Holtz et al. |
| D820,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,376,655 B2 | 8/2019 | Pupke et al. |
| D859,125 S | 9/2019 | Weagle et al. |
| 10,758,684 B1 | 9/2020 | Vitello et al. |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |

(56) References Cited

U.S. PATENT DOCUMENTS

| | | |
|---|---|---|
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0182686 A1 | 7/2015 | Okihara |
| 2015/0191633 A1 | 7/2015 | De Boer et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0319438 A1 | 11/2017 | Davis et al. |
| 2017/0354792 A1 | 12/2017 | Ward |
| 2018/0001540 A1 | 1/2018 | Byun |
| 2018/0078684 A1 | 3/2018 | Peng et al. |
| 2018/0089593 A1 | 3/2018 | Patel et al. |

FOREIGN PATENT DOCUMENTS

| | | |
|---|---|---|
| WO | WO 2008000279 | 1/2008 |
| WO | WO 2017086607 | 5/2015 |

\* cited by examiner

TAMPER EVIDENT CLOSURE ASSEMBLY FOR A MEDICAL DEVICE

CLAIM OF PRIORITY

This is a Non-Provisional patent application that claims priority pursuant to 35 U.S.C. Section 119(e) to a currently pending and prior filed Provisional patent application, namely, that having Ser. No. 62/478,867 filed on Mar. 30, 2017.

BACKGROUND OF THE INVENTION

Field of the Invention

The present invention is directed to a tamper evident closure assembly for a syringe or other medical device, and comprises a housing having an open end and a tip cap removably disposed therein. The tamper evident closure assembly of this invention also comprises an indicator member that is removably disposed in at least partially covering relation to the open end of the housing, and wherein a removal of the tip cap, when attached to the syringe or other medical device, results in a captured disposition of the indicator ring on the syringe or other medical device and attached tip cap, thereby providing a clear indication of tampering or use.

Description of the Related Art

In the medical field, it is a relatively common procedure for authorized medical personnel to order a drug or medication which is to be administered by injection or other procedures, including by intravenous (IV) infusion. It is also relatively common procedure for a number of administering devices to be pre-loaded or filled by authorized personnel, whether within the hospital or at another facility and location, which may be generally referred to as a filling station. However, a filling station is typically located in a remote part of the hospital or other facility, relative to the patient care area where the injection is to be administered. Indeed, at large medical facilities, a filling station may resemble a factory on the hospital grounds from which drugs and other fluids are delivered to multiple nursing stations at different locations. Because of the remote location of many nurse's stations relative to a filling station, a fluid or drug loaded administering device is very often given to another person for delivery to a nurse's station for subsequent dosing of the patient by a duly qualified nurse or other medically trained person. As a result, a pre-loaded syringe may travel quite some distance and be handled by several people before it reaches a nurse's station, which raises some concern that the contents of the syringe may be tampered with or cause the sterility of the syringe and/or its contents to be comprises compromised.

Additionally, in the case where a drug has been prescribed that is very expensive or addictive, such as but not limited to morphine, and has been pre-loaded in the syringe or other administering device, there is an increased danger that the pre-loaded syringe or administering device will be tampered with at some point, by a person seeking unauthorized access to the drug. This possibility can present real danger in that such a person might gain access to the prescribed medicine and then, inappropriately and without concern, substitute some other, unauthorized substance in the syringe, which looks like the actual prescribed medicine and dosage. By way of an example only, if saline solution or water or another drug were substituted for a dose of morphine, the patient would not receive the prescribed drug which by itself, could be quite harmful, while the substituted content might potentially also cause extremely serious harm. Thus, there is a problem of knowing if a sealed, pre-loaded syringe or other administering device has, or has not, been exposed to contamination or might otherwise have been compromised by its being tampered with. This and related types of problems have been described in one or more previously issued U.S. patents granted to one of the inventors herein, such as U.S. Pat. No. 5,328,474. Therefore, to overcome the disadvantages and problems of utilizing a pre-filled syringe, a variety of "tamper evident structures" have been designed with a goal of preventing one from accessing the contents of a pre-filled syringe without authorization, or of at least indicating whether such access has been accomplished or attempted.

In addition, in the use of enteral feeding sets, and like medical devices or accessories, it is also important both to maintain sterility and provide an ability to indicate whether there has been any tampering with or unauthorized access. As commonly recognized in the medical and related professions, the term "enteral" relates to the administration of fluid, typically in the form of liquid, into the intestine, or gastrointestinal tract, such as via the mouth, esophagus or through an artificial opening. As referred to herein, various enteral connectors and/or connecting structures exist for medical devices and/or accessories intended for use in enteral applications and it would be helpful to develop a reliable closure for the same which prevents unauthorized access to such medical devices and/or connectors or indicates if tampering has occurred.

Also, with regard to administering fluids to a patient by intravenous (IV) infusion, a variety of IV assemblies are known and are useful in the treatment of a number of medical conditions, as a variety of fluids and/or medicines can be administered to a patient utilizing such assemblies over a prescribed period of time and in controlled amounts. In use, a conventional IV administration assembly typically includes a reservoir or container, in the form of a bottle or flexible material bag, disposed in an elevated, suspended location substantially adjacent to the patient being treated. In addition, the IV fluid flows from the supported and elevated IV bag to the patient by means of elongated, flexible tubing connected at a proximal end to the IV bag and at the other distal end, connected intravenously to the patient by way of a catheter or like structure. IV administering assemblies of this type will often include a luer connector, which may be structured to at least partially define a luer lock connector assembly, as is well known in the medical profession.

In periods of non-use, it is important to maintain such luer connectors in a closed and fluid-sealed condition in order to maintain sterility, and also, to maintain the integrity of the contents of a pre-loaded medical device (whether a syringe, bottle, flexible IV bag, etc.) prior to use. This is also important in order to restrict unauthorized access to the contents of the IV bag or other medical device and/or luer connector associated therewith.

Despite prior attempts to provide a closure to protect a medical device, connector for a medical device and/or the contents of pre-loaded syringes and other administering devices, certain problems still remain in this field of art. As such, there is a need for an improved closure that is capable of providing secure and reliable, fluid-restricting or fluid-sealing connection to the connector of a medical device and/or discharge structure associated with a pre-loaded syringe or other administering device, such as, but not limited to a luer connector or female structure associated with an enteral feeding set. If any such new closure assembly were developed, it should also have structural and operative features able to provide a clear and reliable indication that tampering or attempted tampering with and/or use of the patient administering device has occurred. Also, any such closure assembly should be capable of use, with little or no structural modifications, with a variety of different connectors, fixtures, administering devices, etc. Finally, any such improved closure assembly should also be structurally and operatively reliable, while still remaining cost effective to manufacture and assemble, in order to facilitate widespread use and acceptance throughout the medical profession.

SUMMARY OF THE INVENTION

The present invention is directed to a closure assembly having tamper evident capabilities and structured to be connected to a medical device such as, but not limited to, a syringe that has been pre-loaded with a drug or other medical prescribed substance, or another type of pre-loaded administering device. In addition, the closure assembly of the present invention is structured in one or more embodiments for attachment and/or connection to the medical device in "flow restricting relation" to a discharge port, such as a nozzle associated with the syringe, or other medical device.

The tamper evident closure assembly comprises a housing including an at least partially hollow interior and an open end disposed in direct communication with the hollow interior. In at least one embodiment, the opposite end of the housing is closed and includes structural components such as, but not limited to a "one-way" rotational drive assembly, as set forth in greater detail hereinafter.

The tamper evident closure assembly also comprises a tip cap that is removably disposed within the hollow interior of the housing in accessible relation to the open end of the housing. As indicated above, the tip cap may include different structural features and operational capabilities such as, but not limited to, a "flow restricting" portion or structure. When provided, the flow restricting portion of the tip cap is disposed and structured to engage and be connected to a discharge port, such as a nozzle associated with a syringe, or other discharge structure associated with a medical device with which it is used. As also described, the tamper evident closure assembly is adapted, in one or more embodiments, to be attached to and used in combination with a pre-loaded syringe or other pre-loaded medical device in a manner which protects and restricts access to the contents thereof, while preventing inadvertent flow of fluid contents from the syringe or medical device.

The tamper evident closure assembly of the present invention may additionally comprise a cover connected to the housing at or immediately adjacent to the open end thereof. In preferred embodiments, the cover is cooperatively structured relative to portions of the housing substantially contiguous to the open end thereof, to retain the tip cap within the hollow interior of the housing in an initial position prior to attachment to the discharge port of the syringe or other medical device. More specifically, the cover is cooperatively structured in preferred embodiments relative to the housing to provide for a "snap-fit" connection of the cover on the housing at and or immediately adjacent to the open end. Further, such a snap-fit connection serves to fixedly connect the cover to the housing at the open end, and results in an ability to assemble the closure assembly in an efficient, time-saving manner. That is, a "snap-fit" connection facilitates an easy and efficient attachment of the cover to the open end of the housing during assembly of the invention, and subsequent to the placement of the tip cap within the hollow interior thereof, because it eliminates the need for welding or other methods of fixed attachment during manufacturing of the closure assembly. As a result, such a fixed, snap-fit connection is also extremely advantageous in terms of saving time and reducing labor costs associated with manufacturing and assembling of the closure assembly.

The tamper evident closure assembly of the present invention also comprises an indicator member. In one or more preferred embodiments, the indicator member comprises an indicator ring having a substantially annular configuration. The indicator ring, as well as other configurations of the indicator member, is removably connected to the cover in at least partially overlying and/or covering relation to the open end of the housing. The indicator ring includes an access opening disposed and configured in aligned relation with the tip cap disposed within the housing. Further, the access opening is dimensioned and configured to facilitate access of the medical device, or at least the discharge port or structure thereof, to pass through the access opening into attachment with the tip cap. However, the size and interior dimension of the access opening is smaller than the tip cap, or at least certain portions of the tip cap, thereby preventing passage of the tip cap through the access opening of the indicator member, whether or not the tip cap is attached to the medical device. In more specific terms, the inner diameter or corresponding dimension of the access opening is less than the outer diameter of the base or largest portion of the tip cap. Therefore, when the indicator member or indicator ring is in position in at least partially covering relation to the open end of the housing, because of the smaller dimension of the access opening relative to the tip cap, the indicator member is disposed and structured to restrict removal or passage of the tip cap from the interior of the housing, through the open end thereof. This removal restricting capability of the indicator member exists both before the tip cap is attached to a syringe or other medical device, and after the tip cap (and closure assembly) has been attached to a syringe or other medical device.

As set forth in greater detail hereinafter, when the closure assembly is installed on syringe or medical device, a forced removal of the tip cap from the interior of the housing through the open end, will result in disconnection of the indicator member from the cover. Any such removal or disconnection of the indicator member, in whole or in part, from the housing serves to provide a clear visual indication of an at least attempted tampering with or use of the syringe or medical device. Similarly, if there is any attempt to tamper with the closure assembly by using a tool, instrument, etc., it is also likely to result in a disconnection of the indicator member from the housing, with again, any such removal or disconnection of the indicator member, in whole or in part, from the housing providing a clear visual indication of attempted tampering or use.

Additionally, the closure assembly of the present invention may comprise a frangible connection between the outer circumferential portions of the indicator ring and the inner peripheral surfaces of the cover. More specifically, the indicator member or indicator ring may include an outer circumferential surface that is removably connected to an inner periphery of the cover, and wherein some of the exposed portions of the indicator member and the cover may be substantially co-planar. In one or more embodiments, this frangible connection may comprise a plurality of frangible tabs, collectively disposed along at least a majority of the outer circumference of the indicator member and on an inner periphery of the annular cover, or alternatively, along the entirety thereof. In other embodiments, the frangible connection may comprise an elongated, curvilinear frangible seam as described subsequently herein.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

DETAILED DESCRIPTION OF THE PREFERRED EMBODIMENT

As represented in the accompanying Figures, the present invention is directed to a closure assembly, generally indicated as 10, and structured to have tamper evident capabilities, which prevent or restrict undetected access to the interior and/or contents of a medical device. The closure assembly 10 is structured to be connected to a medical device 100 such as, but not limited to, a pre-loaded syringe or other pre-loaded administering device.

Figure 1:
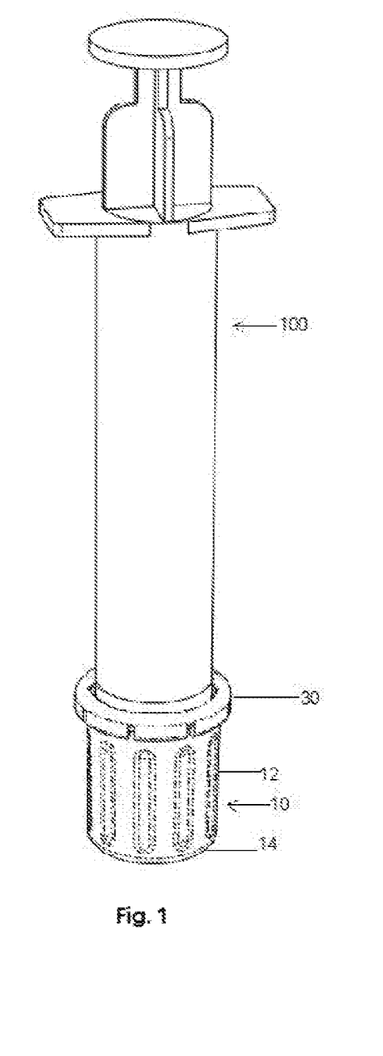
FIG. 1 is an exterior perspective view of a closure assembly according to the present invention, shown as being operatively attached to a medical device.
Figure 2:
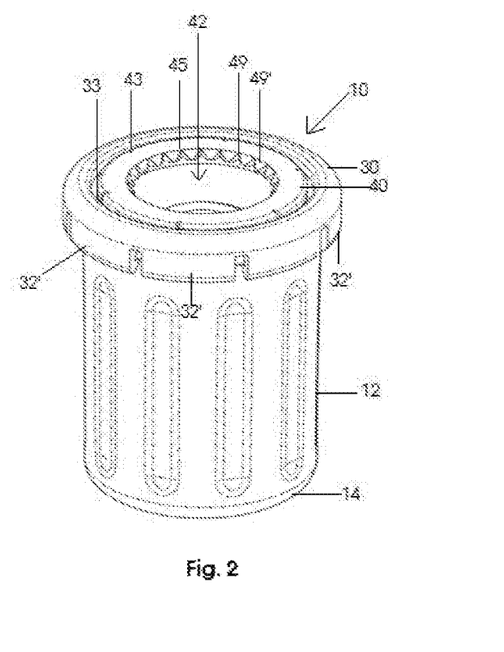
FIG. 2 is also an exterior perspective view of the closure assembly shown in FIG. 1, but in an assembled and unattached state.
Figure 3:
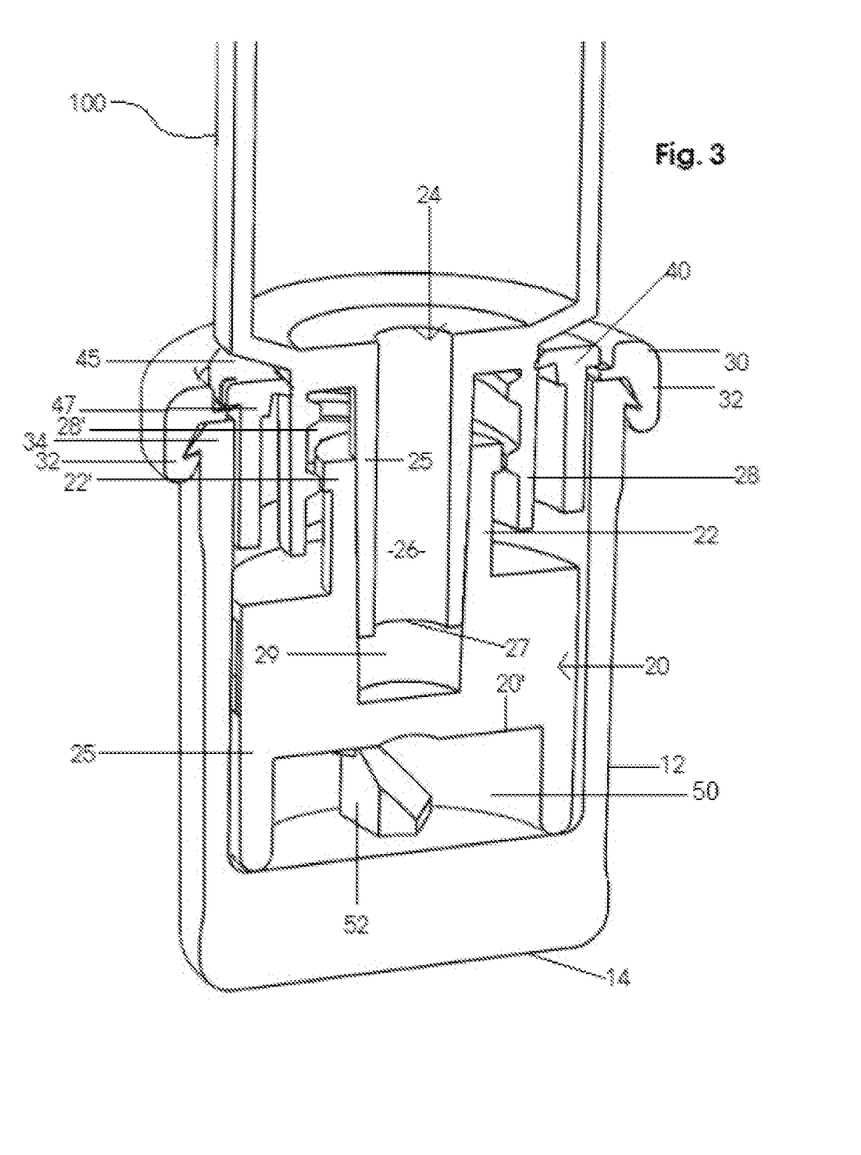
FIG. 3 is a perspective and longitudinal cross section view of the closure assembly shown in FIGS. 1 and 2.
Figure 4:
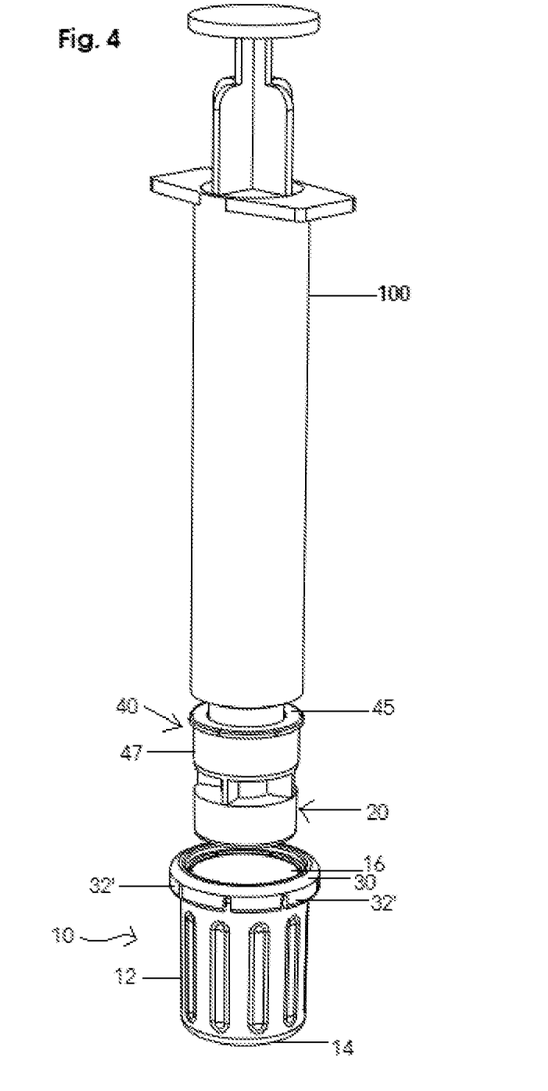
FIG. 4 is a perspective and exploded view of the closure assembly shown in FIGS. 1-3, but illustrating the medical device as being removed from a housing of the closure assembly, and with a tip cap of the closure assembly remaining attached thereto.
Figure 5:
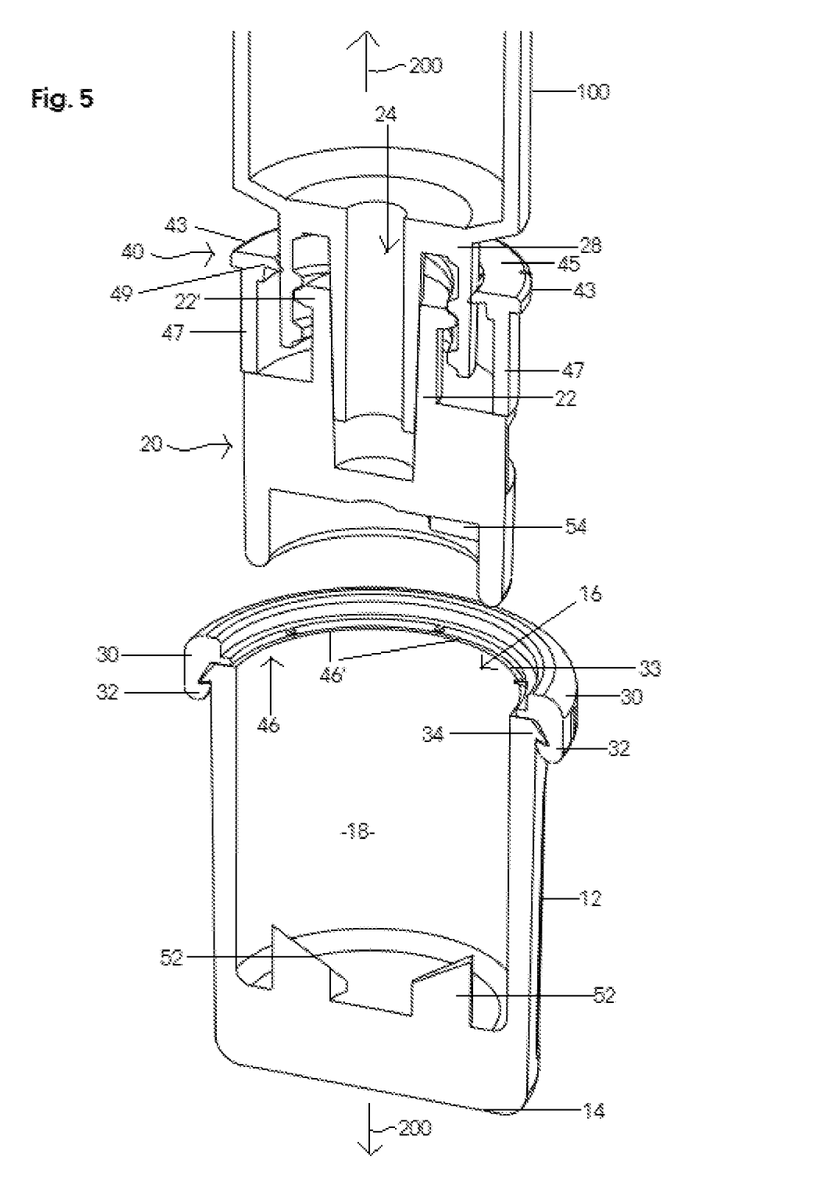
FIG. 5 is an interior, longitudinal and sectional view of the closure assembly and medical device shown in FIG. 4.

With primary reference to FIGS. 1-5, in the illustrated embodiment, the closure assembly 10 comprises a housing 12 having a closed end 14 and an oppositely disposed open end 16, as is perhaps best shown in FIGS. 4 and 5. With reference now to FIG. 5, the housing 12 includes an at least partially hollow interior 18 that is dimensioned and configured to movably and removably contain a tip cap, generally indicated as 20 and best shown in FIG. 3. The tip cap 20 includes a flow restricting portion 22 that is structured and disposed to receive a discharge port 24 or like discharge structure, such as is associated with a pre-loaded syringe 100 or other medical device, when the tip cap 20 and the medical device 100 are attached. As used herein, the term "discharge port" is intended to refer collectively to the discharge structure or portion of a medical device, such as but not limited to a syringe 100 as shown in FIG. 3 that includes a discharge nozzle 25 and has an interior channel 26 with a discharge opening 27. In the illustrated embodiment of the closure assembly 10, the flow restricting engagement between the tip cap 20 and the medical device 100 may include the nozzle 25 and/or other portions of the discharge port 24 being disposed within the receiving channel or chamber 29 of the flow restricting portion 22 of the tip cap 20.

Still referring to the illustrated embodiment of FIG. 3, the syringe 100, including the discharge port 24, also includes a collar 28 having an internally threaded surface 28' disposed in substantially surrounding relation to both the flow restricting portion 22 of the tip cap 20, and the nozzle 25 of the discharge port 24, when the syringe 100 is attached to the tip cap 20. As will be explained in greater detail hereinafter, the internally threaded surface 28' of the syringe collar 28 is structured to establish a threaded connection with a cooperatively configured end or rib 22' of the flow restricting portion 22 of the tip cap 20.

As is also shown in FIGS. 1 through 5, the closure assembly 10 can include a cover 30 connected to the housing 12 adjacent the open end 16 thereof. The cover 30 preferably includes a circular or annular configuration and has a depending skirt 32 disposed and structured to establish a fixed connection with an outer circumferential lip 34 formed on the housing 12 in surrounding, substantially contiguous relation to the open end 16. In a most preferred embodiment, the depending skirt 32 and the circumferential lip 34 are cooperatively configured, dimensioned and structured to define a "snap-fit connection" therebetween. While desirable and not necessarily required, such a snap-fit connection is operative to fixedly secure the cover 30 to the housing 12 adjacent the open end 16. Further, the attachment of the cover 30 to the housing 12, adjacent the open end 16 is facilitated by the snap-fit connection due to an inherent flexibility and bias of the depending skirt 32.

More specifically, and with reference now to at least FIG. 2, the depending skirt 32 of the cover 30 may comprise a plurality of segments 32' integrally connected to a remainder of the cover 30 but disposed in spaced relation to one another. Such a segmented construction facilitates the ability of the plurality of segments 32' to flex outwardly as they are forced over the circumferential lip 34 of the housing 12. However, the plurality of segments 32' are also structured in the most preferred embodiments to include an inherent bias, wherein the depending skirt 32 will return to its original orientation, prior to attachment, and automatically assume an interlocking engagement with the circumferential lip 34 formed on the housing, after the plurality of segments 32' pass over the lip 34 and flex outwardly therefrom. Once in the interlocking connected position, as represented in at least FIGS. 3 and 5, the cover 30 will be fixedly secured to the housing 12 about and/or immediately adjacent to the open end 16. Further, such a fixed, and preferably snap-fit, interlocking engagement may be facilitated by mating portions of the skirt 32 and the circumferential lip 34 both having cooperative structuring, substantially into a "hook" like configuration, as best shown in FIGS. 3 and 5.

Figure 6:
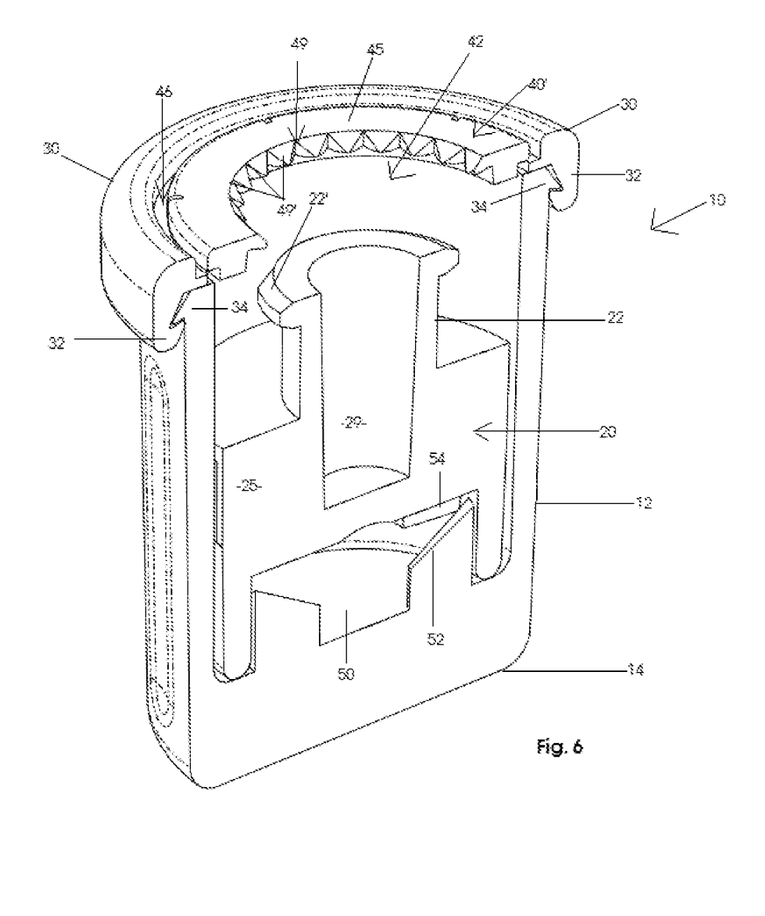
FIG. 6 is an interior, longitudinal sectional view of another embodiment of a closure assembly according to the present invention, which includes a structurally modified indicator member.

The closure assembly 10 of the present invention is also structured to have tamper evident capabilities, as briefly described above. Accordingly, the closure assembly 10 includes an indicator member, generally indicated as 40 in FIGS. 2-5 and as 40' in FIGS. 6-7. The indicator member 40, 40' preferably has an annular or circular configuration thereby defining an indicator ring. The indicator member or ring 40, 40' may further include an exposed portion 45 that is removably connected to the cover 30 in at least partially overlying, covering relation to the open end 16 of the housing 12. In addition, the indicator member or ring 40, 40' includes an access opening generally indicated as 42, as shown in FIGS. 2 and 6, which is disposed in general alignment with the interiorly disposed tip cap 20, specifically including the flow restricting portion 22, as best shown in FIG. 6. Moreover, the access opening 42 is formed in or by the exposed portion 45 and is structured to include a lesser diameter or lesser overall dimension than at least a portion of the tip cap 20 such as the base 25, best shown in FIG. 3. Therefore, the tip cap 20 cannot pass through the access opening 42 of the indicator member or ring 40, 40' and when the closure assembly 10 is in an initial disposition, as shown in FIG. 1 through 3, the tip cap 20 is retained within the hollow interior 18 of the housing 12, due at least in part to the indicator member or ring 40, 40' being disposed in removal restricting relation to the tip cap 20.

Therefore, the indicator member 40, 40' can be described as being in a removal restricting relation to the tip cap 20, both before and after its intended attachment to the syringe 100 or another medical device. In practical terms, before the syringe 100 is attached to the tip cap 20 of the closure assembly 10, the tip cap 20 may be both movably and removably disposed within the hollow interior 18 of the housing 12. The disposition, dimension and overall structuring of the indicator member 40, 40' prevents the tip cap 20 from being inadvertently or purposely removed from the interior 18 of the housing 12, without removal or disconnection of the indicator member 40, 40' from the cover 30. As can be appreciated, any such disconnection of the indicator member or ring 40, 40' will provide a clear indication of tampering or attempted use of the closure assembly 10.

As described above, the indicator member or indicator ring 40, 40' is removably connected to the cover 30 in the illustrated embodiment. In more specific terms, and as shown in FIG. 5, the inner periphery 33 of the cover 30 is removably connected to the outer circumference 43 of the exposed portion 45 of the indicator member or ring 40, 40'. Such a removable interconnection is preferably accomplished by a frangible connection, generally indicated as 46, as also shown in FIG. 5. The frangible connection 46 serves to removably interconnect the inner periphery 33 of the cover 30 and the outer circumference 43 of the indicator ring 40, 40'. As represented in FIG. 5, the frangible connection 46 may be defined by a plurality of frangible tabs 46'. As an alternative embodiment, the frangible connection 46 may be defined by a continuous weakened or frangible seam formed along the inner periphery 33 of the cover 30.

Additionally, and as shown in FIGS. 3 through 5, the indicator member or indicator ring 40 further comprises in the illustrated embodiment, a depending base 47 integrally or otherwise connected to the exposed portion 45. As is perhaps best shown in FIG. 3, the depending base 47 will preferably extend downwardly from the exposed portion 45 of the indicator member 40 and into the hollow interior 18 of the housing 12. The length of the depending base 47 may be such as to be at least minimally spaced from the upper surface of the base 25 of the tip cap 20, as clearly represented in FIG. 3, or may possibly engage the upper surface of the tip cap's base 25 as depicted in FIG. 5. However, it is preferable for the depending base 47 to be disposed a sufficient spaced distance from the base 25 to facilitate movement of the tip cap 20 relative to the discharge port 24 of a syringe 100 when threaded attachment therebetween occurs. As represented in FIG. 3, the attachment of the flow restricting portion 22 of the tip cap 20 to the discharge port 24 or nozzle 25 of syringe 100, serves to position the nozzle 25 into flow restricting relation within the interior of the chamber 29 of the flow restricting portion 22 of tip cap 20.

Figure 7:
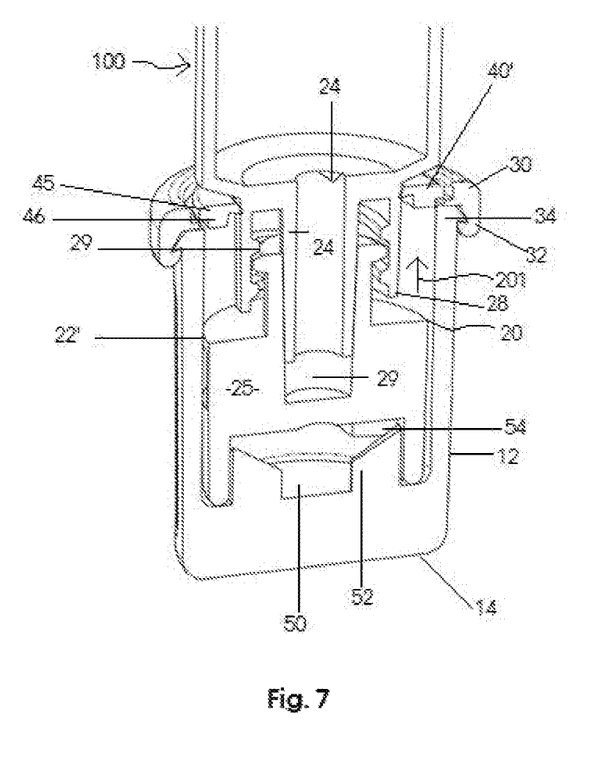
FIG. 7 is an interior, longitudinal sectional view of the embodiment of FIG. 6.
Figure 8:
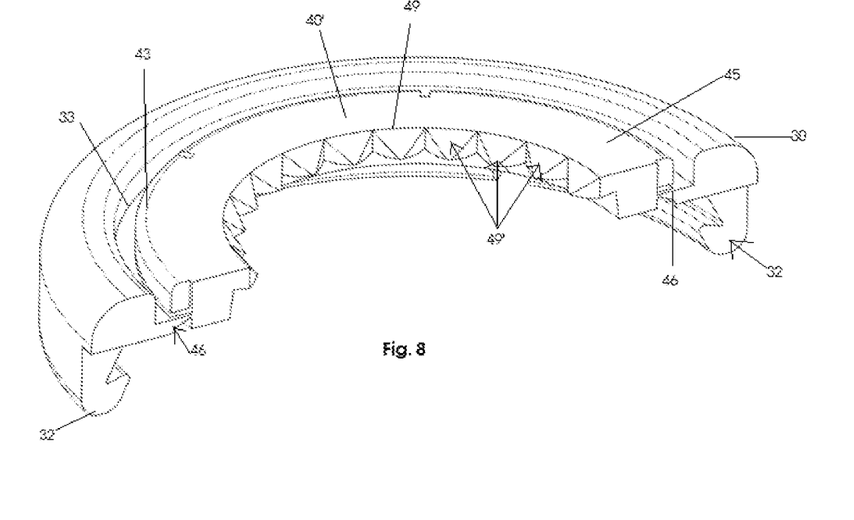
FIG. 8 is a perspective, transverse sectional view in detail disclosing structural details of a cover which may be included in the embodiments of FIGS. 3-5 and 6-7.

With primary reference now to FIGS. 6 and 7, the indicator member or indicator ring 40' is illustrated in another embodiment, and is structured so as to not include a depending base 47. However, most of the other structural and operative features of the indicator member or ring 40' are the same as the indicator member or ring 40 shown in the previous Figures. For example, the indicator member 40' includes an exposed portion 45 that is disposed in substantially coplanar relation to a corresponding portion of the cover 30, and is further disposed in at least partially covering or overlying relation to the open end 16 of the housing 12. Similarly, the exposed portion 45 of the indicator ring 40' is removably connected to the cover 30 by virtue of a frangible connection 46 serving to removably interconnect the inner periphery 33 of the cover 30 (see FIG. 3) to the outer circumference of the indicator ring 40' and/or exposed portion 45 thereof.

Additionally, and as shown in FIGS. 3-5 and 6-7, in both of the illustrated embodiments of the indicator member or ring 40, 40', the access opening 42 is dimensioned to receive at least the discharge port or discharge structure 24 of the syringe 100 there-through into attachment with the tip cap 20. When so attached, the exterior surface portions of the syringe 100 adjacent the discharge port 24 and nozzle 25 thereof, such as the exterior surface portions of the collar 28 shown in FIG. 5, are disposed in engaging relation with the inner peripheral surface portion, generally indicated as 49, of the exposed portion 45 of the indicator member or ring 40, 40'. Further, the inner peripheral portion 49 is structured to include an irregular surface configuration so as to facilitate a secure, snug engagement with the exterior surface of the collar 28 and/or to substantially if not fully eliminate the spacing therebetween. Such an irregular surface configuration may be defined by a plurality of teeth, fingers or similar irregular surface structures 49' extending along at least a majority of the inner peripheral portion 49 or along an entirety thereof.

The purpose and presence of the inner peripheral portion 49 and its relation to the exterior surface of the collar 28, is to prevent or significantly restrict the entry of a tool, instrument, or other tampering device through the access opening 42 of the indicator member or ring 40, and into the hollow interior 18 of the housing 12, when the syringe 100 is attached to the tip cap 20. In turn, this will prevent or restrict access to the drug or other contents of syringe 100 or other medical device to which the closure assembly 10 is attached.

As further represented throughout the accompanying Figures, the closure assembly 10 is initially assembled with the tip cap 20 disposed within the hollow interior 18 of the housing 12, prior to the fixed, snap-fit connection of the cover 30 to the open end 16. In other words, once the tip cap 20 has been inserted into the housing 12, the cover 30 will be fixedly secured to the open end 16 by the preferred snap-fit interlocking connection described previously herein between the depending skirt 32 of the cover 30 and the circumferential exterior lip 34, contiguous to the open and 16. Once assembled, the closure assembly 10 is ready to be attached to a medical device, such as syringe 100 that has been pre-loaded with a drug or other prescribed medical solution. In the illustrated embodiments, the discharge port 24 of the syringe 100 is inserted through the access opening 42 of the indicator member 40 or 40'. Once so inserted, the nozzle 25 or other corresponding portion of the discharge port 24 will pass into the interior chamber or receiving channel 29 of the flow restricting portion 22 of the tip cap 20, thereby establishing a flow restricting connection therebetween.

Additionally, and as perhaps best illustrated in FIG. 3, once the nozzle 25 of the syringe 100 has been inserted through the access opening 42 and into the tip cap 20, the aforementioned threaded connection can be established between the interior threaded surface 28' of the collar 28 and the corresponding end or outwardly extending rib 22' formed on the flow restricting portion 22 of tip cap 20. This threaded connection is facilitated by the provision of a "one-way" rotational drive assembly, generally indicated as 50 and best illustrated in FIGS. 5-7. As shown, in FIGS. 3, and 5-7, the "one-way" rotational drive assembly 50 preferably comprises a "ramp and cliff" drive structure, including ramp and cliff drive components 52 and 54, located both on the interior surface of the closed end 14 of the housing 18, and the inner, undersurface 20' of the tip cap 20. The disposition and structure of the drive components 52 and 54 and their interaction with one another facilitate a free, continuous rotation of the tip cap 20, relative to the housing 12, in one direction, such as a counter clockwise direction. However, due to the structural interaction of the ramp and cliff components 52 and 54, the tip cap 20 is prevented from rotating in the opposite or clockwise direction relative to the housing 12. In turn, this allows the discharge port structure 24 and the threaded surface 29 to rotate relative to the corresponding rib member 22', accomplishing the aforementioned threaded attachment.

Once the closure assembly 10 of the present invention is installed or attached onto a syringe 100 or other medical device, to access or use the contents of the syringe 100, whether authorized or unauthorized, one must exert a pulling force on either the syringe 100 or the housing 12 or both, in the manner schematically represented by the directional arrows 200 shown in FIG. 5. Such a pulling or axially directed force 200 will result in movement of the tip cap 20 and the attached medical device 100 outwardly towards and through the open end 16 of the housing 12. However, due to the fact that the indicator member 40, 40' is disposed in removal restricting relation to the tip cap 20, and the fact that the tip cap 20 is too large to pass through the access opening 42 of the indicator member 40, the base 25 of the tip cap 20 will come into disconnecting engagement with the tip 40, 40' causing the rupture or detachment of the frangible connection 46.

In more specific terms, and with regard to the embodiment of FIGS. 3 and 5 corresponding portions of the base 25 of the tip cap 20 will move into engagement with the innermost end of the base 47 of the indicator member or ring 40, as clearly demonstrated in FIG. 5. When the force 200 is continuously applied, the indicator member or ring 40 will be detached from the cover 30 along the aforementioned frangible connection 46. Further, the indicator member 40, will then become captured on or about the medical device 100, such as around the collar 28 and the tip cap 20, as clearly represented in FIG. 5.

With regard to the embodiment of FIGS. 6 and 7, wherein the indicator member or ring 40' is absent the elongated depending base 47, a similar procedure will occur. More specifically, as an axial or pulling force 200 is exerted on the housing 12 and/or the medical device 100, when the tip cap 20 is attached to the medical device 100 within the housing 12, the tip cap 20 will move from its internal disposition outwardly towards and through the open end 16 of the base 12. This will cause a disconnecting engagement between the base portion 25 of the tip cap 20 and the under portion 45' of the normally exposed portion 45 of the indicator member or indicator ring 40', as indicated by directional arrow 201 in FIG. 7. Similarly, when the tip cap 20 and the attached medical device 100 exit the interior 18 of the housing 12, the indicator member or indicator ring 40' will be disposed in the captured position on the medical device 100, as with the embodiment of FIG. 5, generally about the exterior of the collar 28 and between the exterior of the discharge port 24 and the base 25 of the tip cap 20.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure assembly for a medical device, said closure assembly comprising:
   a housing including an at least partially hollow interior and an open end,
   a tip cap removably disposed within said hollow interior,
   a cover connected to said housing adjacent said open end,
   an indicator member removably connected to said cover and disposed in at least partially covering relation to said open end,
   said indicator member including an access opening disposed and dimensioned to facilitate passage of at least a portion of the medical device therethrough into attachment with said tip cap,
   said access opening being sufficiently smaller than said tip cap to prevent passage of at least a portion of said tip cap there through, and
   said tip cap disposed and dimensioned to engage and disconnect said indicator member from said cover concurrent to removal of said tip cap and attached medical device through said open end.

2. The closure assembly as recited in claim 1 wherein said indicator member is at least initially connected to said cover in removal restricting relation to said tip cap, concurrent to said connection of said cover to said housing.

3. The closure assembly as recited in claim 2 wherein said indicator member is removably connected to an inner periphery of said cover in interruptive relation to passage of said tip cap through said open end.

4. The closure assembly as recited in claim 3 wherein said indicator member comprises an indicator ring, said indicator ring comprising an outer circumference removably connected to said inner periphery of said cover.

5. The closure assembly as recited in claim 4 further comprising a frangible connection disposed in removable interconnecting relation between said outer circumference of said indicator ring and said inner periphery of said cover.

6. The closure assembly as recited in claim 2 wherein said cover is fixedly connected to said housing at said open end.

7. The closure assembly as recited in claim 6 wherein said cover includes an exterior depending skirt cooperatively structured and configured with an outer circumferential lip of said housing to define a snap-fit connection therebetween.

8. The closure assembly as recited in claim 7 wherein said snap-fit connection is further defined by said depending skirt of said cover and said circumferential lip of said housing comprising cooperatively disposed and configured hook structures.

9. The closure assembly as recited in claim 7 wherein said depending skirt comprises a flexible, inherently biased construction.

10. The closure assembly as recited in claim 9 wherein said flexible, inherently biased construction comprises said depending skirt including a plurality of integrally interconnected, spaced apart segments collectively extending along at least a majority of a length of said depending lip.

11. The closure assembly as recited in claim 7 wherein said circumferential lip is disposed in surrounding, substantially contiguous relation to said open end.

12. The closure assembly as recited in claim 1 wherein said indicator member comprises an indicator ring, said indicator ring including an inner peripheral portion defining said access opening; said inner peripheral portion disposed in engaging relation with the medical device concurrent to the attachment of said tip cap and the medical device, within said housing.

13. The closure assembly as recited in claim 12 wherein said inner peripheral portion comprises an irregular surface configuration extending along at least a majority of a length thereof.

14. The closure assembly as recited in claim 13 wherein said irregular surface configuration comprises a plurality of teeth collectively extending along at least a majority of the length of said indicator ring.

15. The closure assembly as recited in claim 12 wherein said indicator ring is removably connected to an inner periphery of said cover; said indicator ring including an elongated, depending base initially disposed within said housing in an interruptive engaging disposition to passage of said tip cap through said open end.

16. The closure assembly as recited in claim 1 wherein said indicator member comprises an indicator ring disposed in a surrounding captured disposition on the medical device subsequent to said disconnecting engagement of said tip cap with said indicator ring.

17. The closure assembly as recited in claim 1 wherein said access opening of said indicator member includes a smaller inner diameter than an outer diameter of said tip cap.

18. A closure assembly for a medical device, said closure assembly comprising:
   a housing including an open end and an at least partially hollow interior;
   a tip cap movably and removably disposed within said hollow interior,
   a cover connected to said open end of said housing and including an indicator ring removably connected thereto and disposed in at least partially covering relation to said open end,
   an access opening disposed and dimensioned to facilitate passage of a portion of the medical device therethrough into attachment with the tip cap,
   said indicator ring disposed in interruptive, removal restricting relation to said tip cap, relative to said open end,
   said tip cap disposed and dimensioned to engage and disconnect said indicator ring from said cover, concurrent to removal of said tip cap and attached medical device through said open end, and
   said indicator ring disposed in a surrounding, captured disposition on the attached medical device, subsequent to said disconnection of said indicator ring from said cover.

19. The closure assembly as recited in claim 18 wherein said access opening of said indicator member includes a smaller inner diameter than an outer diameter of said tip cap.

20. The closure assembly as recited in claim 18 wherein said indicator ring includes an outer circumference removably connected to an inner periphery of said cover.

21. The closure assembly as recited in claim 20 further comprising a frangible connection disposed in removable, interconnecting relation between said outer circumference of said indicator ring and an inner periphery of said cover.

22. The closure assembly as recited in claim 18 wherein said cover and said housing are cooperatively structured to define a snap-fit connection therebetween; said snap-fit connection defined by an interlocking fixed connection of said cover to said housing at said open end.

23. The closure assembly as recited in claim 18 wherein said indicator ring includes an inner peripheral portion defining said access opening; said inner peripheral portion disposed in engaging relation with the medical device concurrent to the attachment of said tip cap and the medical device, within said housing.

24. The closure assembly as recited in claim 23 wherein said inner peripheral portion comprises an irregular surface configuration extending along at least a majority of a length thereof.

25. The closure assembly as recited in claim 18 wherein said indicator ring comprises an exposed portion disposed in at least partially covering relation to said open end and an elongated base connected to and depending from said exposed portion initially into said housing in an interruptive disposition to passage of said tip cap through said open end.

26. The closure assembly as recited in claim 18 wherein said tip cap comprises a one-way directional drive assembly comprising a ramp and cliff structure and a flow restricting portion disposable in flow restricting relation to a discharge port of the medical device.

* * * * *